(12) United States Patent
Merchez et al.

(10) Patent No.: US 8,575,568 B2
(45) Date of Patent: Nov. 5, 2013

(54) ELECTROOPTIC MEASUREMENT DEVICE AND METHOD INTENDED FOR CLASSIFYING AND COUNTING MICROSCOPIC ELEMENTS

(75) Inventors: Benoit Merchez, Le Pouget (FR); Patrick Brunel, Le Cres (FR); Philippe Nerin, Nages (FR)

(73) Assignee: Horiba ABX SAS, Montpellier (FR)

( * ) Notice: Subject to any disclaimer, the term of this patent is extended or adjusted under 35 U.S.C. 154(b) by 203 days.

(21) Appl. No.: 12/997,705

(22) PCT Filed: Jun. 25, 2009

(86) PCT No.: PCT/FR2009/051216
§ 371 (c)(1),
(2), (4) Date: Dec. 13, 2010

(87) PCT Pub. No.: WO2010/004173
PCT Pub. Date: Jan. 14, 2010

(65) Prior Publication Data
US 2011/0089340 A1    Apr. 21, 2011

(30) Foreign Application Priority Data

Jun. 25, 2008 (FR) .................................. 08 54229

(51) Int. Cl.
*G01J 1/58* (2006.01)
*G01N 21/00* (2006.01)
*G01N 21/49* (2006.01)

(52) U.S. Cl.
USPC ................... 250/458.1; 250/573; 356/432

(58) Field of Classification Search
USPC ................. 250/458.1, 573; 356/432
See application file for complete search history.

(56) References Cited

U.S. PATENT DOCUMENTS

| | | | |
|---|---|---|---|
| 3,710,933 A | 1/1973 | Fulwyler et al. | |
| 4,745,285 A | 5/1988 | Recktenwald et al. | |
| 5,138,181 A | 8/1992 | Lefevre et al. | |
| 5,408,307 A | 4/1995 | Yamamoto et al. | |
| 6,524,858 B1 | 2/2003 | Zelmanovic et al. | |
| 6,897,954 B2 | 5/2005 | Bishop et al. | |
| 6,934,014 B1* | 8/2005 | Kleinhuber | 356/72 |
| 7,423,751 B2* | 9/2008 | Hairston et al. | 356/318 |
| 2006/0004530 A1 | 1/2006 | Miyamoto et al. | |
| 2006/0219873 A1 | 10/2006 | Martin et al. | |
| 2010/0324834 A1* | 12/2010 | Treptow et al. | 702/32 |

FOREIGN PATENT DOCUMENTS

| | | |
|---|---|---|
| EP | 0 425 381 | 5/1991 |
| EP | 0 533 333 | 3/1993 |
| EP | 0 806 664 | 11/1997 |
| EP | 0 856 735 | 8/1998 |
| EP | 1 431 745 | 6/2004 |
| EP | 1 710 558 | 10/2006 |

(Continued)

*Primary Examiner* — David Porta
*Assistant Examiner* — Faye Boosalis
(74) *Attorney, Agent, or Firm* — Clark & Brody

(57) ABSTRACT

The invention relaters to a device (100) for biological analysis by measurement of photoluminescence in a fluid in a measurement tank (111). This device (100) comprises at least two light sources (121, 131) adapted to emit in different spectral areas respectively appropriate for measurement of absorption and fluorescence, and a sensor device (140) comprising a sensor (141), an optical system (142), and filter means (144), which three elements are mutualized in accordance with the invention to enable absorption and/or fluorescence to be measured. In accordance with the invention the internal gain of the sensor (141) is configurable to enable the fluorescence and absorption measurements to be executed sequentially.

14 Claims, 5 Drawing Sheets

(56) References Cited

FOREIGN PATENT DOCUMENTS

| FR | 2 873 813 | 2/2006 |
|---|---|---|
| GB | 2 125 181 | 2/1984 |
| WO | 2006/053960 | 5/2006 |
| WO | 2006/086382 | 8/2006 |
| WO | 2008/019448 | 2/2008 |

* cited by examiner

ELECTROOPTIC MEASUREMENT DEVICE AND METHOD INTENDED FOR CLASSIFYING AND COUNTING MICROSCOPIC ELEMENTS

BACKGROUND OF THE INVENTION

The field of the present invention is that of biological analysis, in particular hematological analysis. The invention relates to the general field of devices and methods for electro-optic measurements in a fluid present in a measuring tank. Such devices and methods are intended in particular for classifying and counting microscopic objects in a fluid, for example a biological fluid.

To be more precise, the invention relates to devices that use analysis methods based on using electrical and optical measurements to count and distinguish cells present in a sample to be analyzed. In the context of the present invention, this is preferably a blood sample.

With hematopoietic cells, the person skilled in the art knows that volumetric or diffractometric morphological analysis of the cell, including the phenomena of extinction or absorption, enables discrimination of the main cell lines includes erythrocytes (red cells), thrombocytes (platelets), and leucocytes (white cells). The white cell population is itself divided into a plurality of categories such as lymphocytes, monocytes, neutrophils, eosinophils, and basophils.

The maturity of these cells can to some extent be determined by determining simultaneously their volume and their apparent absorption of white light, as described in U.S. Pat. No. 5,138,181 filed by the Applicant. A device using quasi-monochromatic light is described in the patent WO 2006/053960.

This assessment of cellular maturity is very important because it enables early diagnosis. Generally speaking, most cells present in the circulating blood are mature cells.

For each of the above-mentioned cell types, the various levels of maturity are known. Thus red cells, also called erythrocytes, are first produced in the form of proerythroblasts, then basophilic erythroblasts, then polychromatophilic erythroblasts which evolve into acidophilic erythroblasts, then into reticulocytes. It is these reticulocytes that finally differentiate into erythrocytes once they have entered the circulating blood.

White cells, also called leucocytes, are also first produced in the bone marrow in the preliminary myeloblast form. These myeloblasts thereafter yield the progranulocyte that is then transformed into basophilic, eosinophilic or neutrophilic granulocyte, at first non-segmented and then with a nucleus that segments increasingly with age.

The same myeloblasts are also the source of the monocyte line that yields the monoblasts, promonocytes and then monocytes that enter the peripheral circulation.

The stem cells from which the myeloblasts originate also give rise to the lymphocyte line through a differentiation in lymphoid stem cell form, part of which line continues to mature in the thymus and the ganglions (line T) and the remainder remains in the bone marrow in order to yield the B lymphocyte line. The same B lymphocytes that, once activated in the form of plasmocytes, produce the antibodies to combat pathogenic antigens.

Blood platelets, also called thrombocytes, are derived from the megacaryoblasts, themselves stemming from the myeloid progenitor from which originate the myeloblasts which, on reaching the final stage of their maturation (thrombocytogen megacaryocytes) produce platelets by splitting their cytoplasm. The recent platelets (reticulated platelets) contain RNA that is the residue of the original cell.

The diagnosis of some pathologies requires the increasingly refined counting of hematopoietic cells. In particular, it becomes necessary to be able to show up new populations such as reticulocytes and erythroblasts that are the immature versions of erythrocytes. Similarly, showing up immature cells, precursors of the leucocytes, called immature lymphocytes, monocytes or granulocytes is of great importance. Likewise, classifying and counting the activated lymphocytes or reticulated platelets would make it possible to obtain a meaningful improvement in the diagnosis of patients.

Since the mean lifetime of a red cell is 120 days, the normal regeneration rate must therefore be 0.83%. The normal mean percentage generally accepted is in the range 0.5% to 1.5%, these values being higher (from 2% to 6%) in the neonate of less than 3 weeks. Observing and counting the reticulocytes is thus an indicator of erythropoietic activity and thus a parameter that is especially useful, in particular in monitoring medullary regrowth after chemotherapy, in follow-up treatment by recombinant erythropoietin (rHuEpo), in the anemia exploratory balance or in searching for a hemolysis or compensated hemorrhagia.

A few examples of pathologies in which differentiating and counting cells in this way are useful are given below.

The clinical benefit of counting erythroblasts may prove important for detecting certain forms of anemia, for example. The common characteristic of hemolytic anemia is the excess destruction of adult erythrocytes that may result from extra-corpuscular factors or intrinsic anomalies of the structure or function of the erythrocytes.

Erythroleukemia is a variety of acute myeloblastic leukemia that is characterized by malignant proliferation of cells of the red line and precursors of the granular line. From the cytological point of view, peripheral hyperleucocytosis is noted at the initial stage with circulating blasts present (59%). The myelemia corresponds to the passage into the circulating blood of immature elements, the granular line or the erythrocyte line.

On the subject of differentiation, reticulocytes constitute one of the most interesting cell families and numerous methods exist and are under development in automated hematological analysis. These cell lines may be counted by marking nucleic acids by means of fluorescent coloring agents, for example asymmetrical cyanines, and in particular Thiazole Orange.

This molecule has unique physico-chemical characteristics for intra-cytoplasmic detection of nucleic acids (RNA or DNA). When free in solution, this molecule exhibits very little fluorescence induced by photo-excitation. The stereochemical configuration of Thiazole Orange is such that this molecule is interleaved between the bases of the nucleic acids. In this state the molecule fluoresces. Thus detecting and measuring the level of fluorescence makes it possible to quantify intra-cytoplasmic nucleic acids. The nature of the cells may be deduced from this quantification of intracytoplasmic nucleic acids combined with a second optical or electrical measurement, thus enabling them to be counted absolutely or relatively.

Existing electro-optic devices for measuring this fluorescence are relatively complex. They use considerable hardware resources, especially if high analysis rates are expected. In this situation, it is relatively standard practice to use a laser light source with a set of sensors for measuring diffraction, generally identified by the abbreviations FSC (forward scattering) and SSC (side scattering), or extinction, generally identified by the abbreviation ALL (axial light loss).

The same laser makes it possible to induce fluorescence of the marker or markers or the coloring agent or agents present on or in the cell at the moment of crossing the laser beam. In the standard manner, fluorescence light and diffraction light are separated on the basis of their spectral properties. To this end, multi-dielectric interference optical filters are generally used, i.e. filters obtained by the alternate deposition of two or more transparent materials having different refractive indices. To measure fluorescence photomultipliers or photodiodes are used that most of the time operate in avalanche mode. These systems are relatively complex from the optical and mechanical points of view.

US patent application 2006/0219873 discloses the use of an AGC (automatic gain control) avalanche photodiode. This device is used in a flow cytometer in which the gain of the photodiode is adjusted automatically as a function of the applied voltage.

Patent application EP 1 710 558 in the name of Sysmex discloses a plurality of sensors for recovering data from each light source. This device also effects only SSC measurements.

Patent application EP 0 533 333 discloses an on-line reader device in which the cells are not analyzed when flowing. Again, even though data may be obtained (absorption, fluorescence, reflectance data), the data is not obtained with a single sensor.

Patent application WO 2008/019448 discloses an epifluorescence device with no absorption reading.

Patent application EP 0 806 664 uses a plurality of sensors if it is necessary to obtain data from a plurality of different sources.

U.S. Pat. No. 4,745,285 discloses a device capable of counting particles marked with a plurality of fluorochromes. This device has a single-wavelength light source and a plurality of sensors capable of recovering the data of each fluorescence.

U.S. Pat. No. 5,408,307 discloses a device able to effect FSC, SSC and fluorescence measurements using plurality of different sensors.

U.S. Pat. No. 6,897,954 (Becton Dickinson and Co), describes the use of a plurality of fluorescences associated with a plurality of photosensors to count cells when flowing. The gain of each photosensor may be modulated in order to adjust it to the fluorescence detected.

None of the known devices integrates the electro-optical and opto-fluidic measuring systems necessary for differentiating and counting biological cells, in particular those in the circulating blood. The size and complexity of the existing devices make them costly and complex to operate.

OBJECT AND SUMMARY OF THE INVENTION

Thus the principal object of the present invention is to alleviate such drawbacks by proposing a device for biological analysis by electro-optical measurements on a fluid in a measurement tank, this device comprising at least two light sources adapted to emit in different spectral areas respectively appropriate for measurement of absorption and fluorescence, a device for measuring the impedance associated with each absorption and fluorescence measurement, and a shared sensor device comprising a sensor, an optical system, and filter means, which three elements are mutualized to enable the absorption and/or fluorescence to be measured, the internal gain of the sensor being configurable to enable the fluorescence and absorption measurements to be executed sequentially.

The set-up is configured so that fluorescence is measured by the optics and the sensor used to measure absorption. This approach leads to an optimum level of integration that is characteristic of the invention. Advantages of this invention include reduced production costs and easy implementation.

With such a device, each cell may be measured in a "double measurement" mode, namely, a resistivity measurement together with an absorbance and/or fluorescence measurement. A resistivity measurement associated with an absorbance or a fluorescence measurement enables volumetric information to be obtained.

The apparent absorption largely involves cellular refringence/diffraction phenomena. The above measurements obtain sufficient reliable data to obtain sensitive results specific to the set of cell populations.

The invention proposes an original and simplified optical set-up enabling reading of cell suspensions chemically prepared beforehand using reagents having a specific function. These cellular suspensions are analyzed sequentially using a volumetry-absorption reading and a volumetry-fluorescence measurement, i.e. a two-parameter electro-optical measurement performed by the same sensor device.

This double measurement greatly simplifies the hardware resources. The device of the invention thus enables classification and counting of the following, for example: platelets, red cells, lymphocytes, monocytes, neutrophils, eosinophils, basophils, reticulocytes, erythroblasts, reticulated platelets, immature lymphocytes, immature monocytes, immature granulocytes, activated lymphocytes and non-segmented neutrophils.

In one embodiment of the invention the sensor is an avalanche photodiode connected to a bias circuit adapted to inhibit the internal avalanche gain.

The use of a simple avalanche photodiode in a particular bias context novel to the invention enables simple and effective implementation of the invention at relatively low cost.

In an advantageous embodiment of the invention, the inhibited internal gain is 1, with the avalanche photodiode behaving as a simple photodiode.

This embodiment reduces the behavior of the avalanche photodiode to that of a standard photodiode as used conventionally for absorption measurements. In the absence of the gain inhibition provided by the invention, the avalanche photodiode would immediately saturate if used for absorption measurement at high light intensity.

In one embodiment of the invention, the bias circuit comprises a two-position switch providing two different voltages, a high voltage and a low voltage, and digitally controlled to provide the high voltage or the low voltage for biasing the photodiode.

Through simple switched control, this embodiment of the invention offers very robust operation. The diode is successively biased with a high voltage and a low voltage as a function of the position of the switch. This modifies the internal gain and thus the sensitivity of the receiver.

In another embodiment of the invention, the bias circuit comprises a programmable voltage generator or a voltage generator controlled by digital or analog means to control the bias voltage applied by this generator to the avalanche photodiode.

This other embodiment enables a single voltage generator to be used.

According to one particular feature of the invention, the two light sources have emission optical axes coplanar with the optical axis of the light sensor.

In absorption mode, the optical device conjugates three planes, that of the entry pupil, that across which the cells pass, and that of the reception pupil. The illumination is thus Newtonian. Here the optics are corrected for third order aberrations, namely to correct geometrical and chromatic aberrations introduced by the plane, water and glass, refracting surfaces of the measurement chamber. All optical paths significant for the measurements are then coplanar.

According to an advantageous feature of the invention, the optical axis of the light source emitting at the absorption wavelengths is aligned with that of the light sensor and the optical axis of the light source for exciting fluorescence is perpendicular to the optical axes of the sensor and the other light source.

This feature provides the sensor device with good absorption and fluorescence behavior. For absorption measurements the sensor device is situated facing the light source. For fluorescence measurements, placing the source perpendicular to the sensor device, prevents the emission light interfering with the measurement of the lower intensity fluorescence.

According to another particular feature of the invention, the marker used for fluorescence being Thiazole Orange, the fluorescence excitation source must emit at around 470 nanometers (nm) and the filter means of the sensor device must include a colored filter cutting off at 495 nm.

Using Thiazole Orange is known to be advantageous for discriminating a plurality of cell populations. In the context of the invention, it allows the use of a relatively low cost colored glass filter. Such an inexpensive filter is available for only certain types of bandwidth. Thiazole Orange still has some efficacy even when excited below its maximum excitation secondary situated at 488 nm. The inventors have thus discovered that the combination of excitation of Thiazole Orange at a wavelength around 470 nm with the use of a colored glass filter available at relatively low cost makes it possible to perform an entirely pertinent quantitative fluorescence measurement, i.e. a sensitive and specific measurement, with an avalanche photodiode or a sensor of high internal gain. This discovery is used in a particular way by the invention which further makes it possible to perform an absorption measurement with the avalanche diode.

The sensor is advantageously connected to an electronic amplification stage with electronic gain variable as a function of the measurement effected.

Using an electronic amplification stage adds the possibility of a quantification improvement in luminous intensity by maximizing the use of the available dynamic range for subsequently processing the data.

According to one application feature of the invention, the internal gain of the sensor and the electronic gain are configurable to enable discriminating absorption and fluorescence measurements for a plurality of cell populations chosen from basophils, lymphocytes, monocytes, neutrophils, eosinophils, red blood cells (erythrocytes), platelets, erythroblasts, red blood cell precursors, reticulocytes, and reticulated platelets.

This feature offers some latitude in adapting the device to measure the different types of cells to be counted. This latitude makes it possible to modify the sensitivity of the sensor device and the use of a data processing dynamic range as a function of the cell type.

In particular, the internal gain of the sensor and the electronic gain are advantageously configurable to enable, with the sensor device, discriminating absorption and fluorescence measurements for each analysis cycle.

Here an analysis cycle means each cycle of use of the device for classification and absolute counting of a family of cells present in the sample.

This also corresponds to the process involving incubation of the sample to be analyzed with a particular reagent and other parameters, for example the speed at which cells enter the measurement tank. It is therefore possible, in the present context, to perform five different analysis cycles, for example. The LMNE cycle corresponds to the analysis cycle enabling accurate classification and counting of lymphocytes, monocytes, neutrophils, and eosinophils. The GR/PLT cycle makes possible absolute counting of erythrocytes and platelets. The BASO cycle makes it possible to distinguish and count basophils. The RETIC cycle makes it possible to distinguish and count reticulocytes, which are the precursors of red cells. The ERB cycle makes it possible to count precursors of these reticulocytes, namely erythroblasts.

The internal gain of the sensor and the electronic gain are advantageously configurable to enable, with the sensor device, discriminating absorption and fluorescence measurements for at least basophils and reticulocytes.

This feature makes it possible to cover the spectrum of mean luminous intensities observed for each of the cell types referred to above. The fluorescent luminous intensity is lowest during the RETIC cycle. The sensitivity of the sensor must therefore be the maximum sensitivity. In contrast, basophils are revealed by an absorption measurement in a configuration in which the luminous intensity is the highest. During the BASO cycle, the sensitivity of the sensor must therefore be a minimum sensitivity. By ensuring that these two types of extreme cells are counted, it is bound to be possible to adjust the device for other cell types by modifying the internal gain of the sensor and the electronic gain.

According to a further additional feature of the invention, the two sources may be turned on simultaneously to obtain biochemical and morphometric data.

BRIEF DESCRIPTION OF THE DRAWINGS

Other features and advantages of the present invention emerge from the following description given with reference to the appended drawings, which show one non-limiting embodiment of the invention. In the figures.

DETAILED DESCRIPTION OF AN EMBODIMENT OF THE INVENTION

Figure 1:
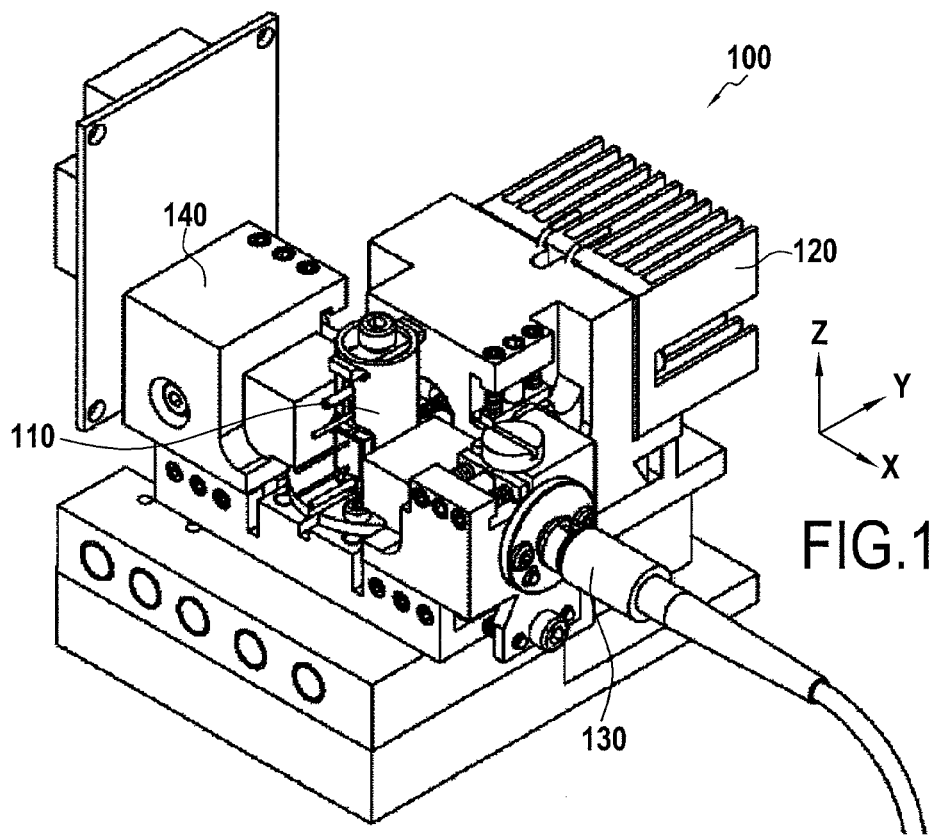
FIG. 1 is a perspective view of a device of the invention.

FIG. 1 is a perspective view of a preferred embodiment of a device 100 of the invention. This device 100 consists of four functional assemblies: an assembly 110 supporting the measurement tank, two assemblies 120 and 130 supporting light sources, and an assembly 140 supporting the light sensor. In the embodiment of the invention shown, the two assemblies 120 and 130 supporting the light sources are mutually perpendicular, one of the two facing the assembly 140 carrying the sensor.

Figure 2:
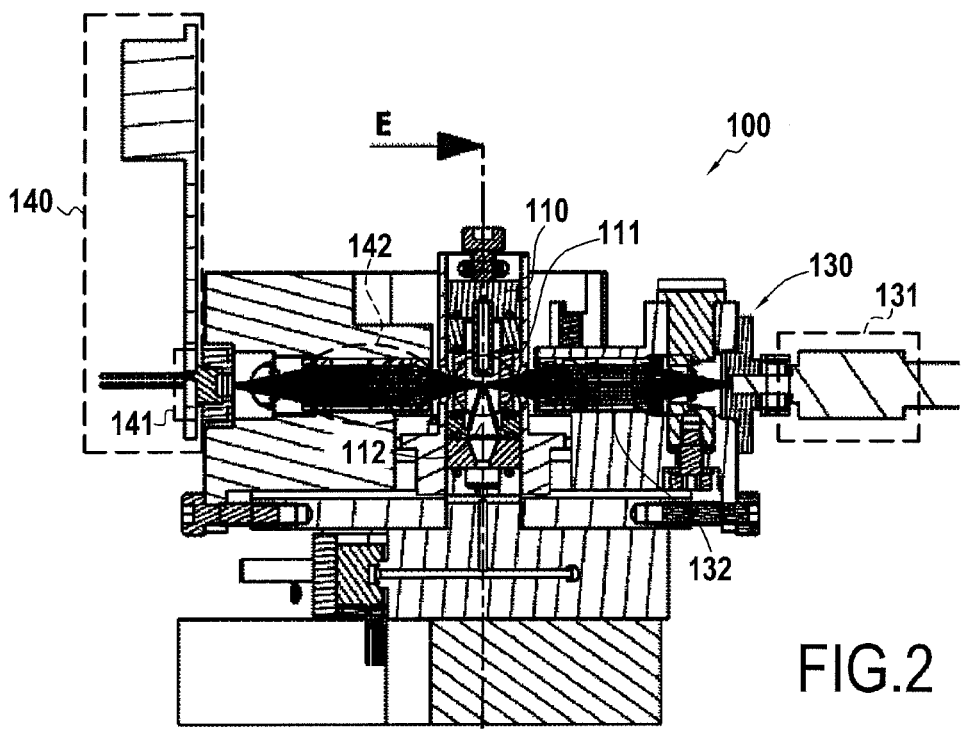
FIG. 2 is a view in section (XZ) of the device from FIG. 1.

FIG. 2 is a section of the device 100 on a plane XZ intersecting the measurement plane. The assembly 110 comprises a measuring tank 111 and a nozzle 112 discharging into the measuring tank 111 in order to generate therein the flow of fluid to be analyzed in accordance with the principles of flow cytometry. The assembly 130 comprises a light source 131 and optics 132 providing suitable illumination of the measurement tank.

The assembly 140 comprises a sensor 141 and optics 142 for appropriate reception of light by the sensor 141. The optical axes of the assemblies 130 and 140 are perpendicular to the flow direction.

Figure 3:
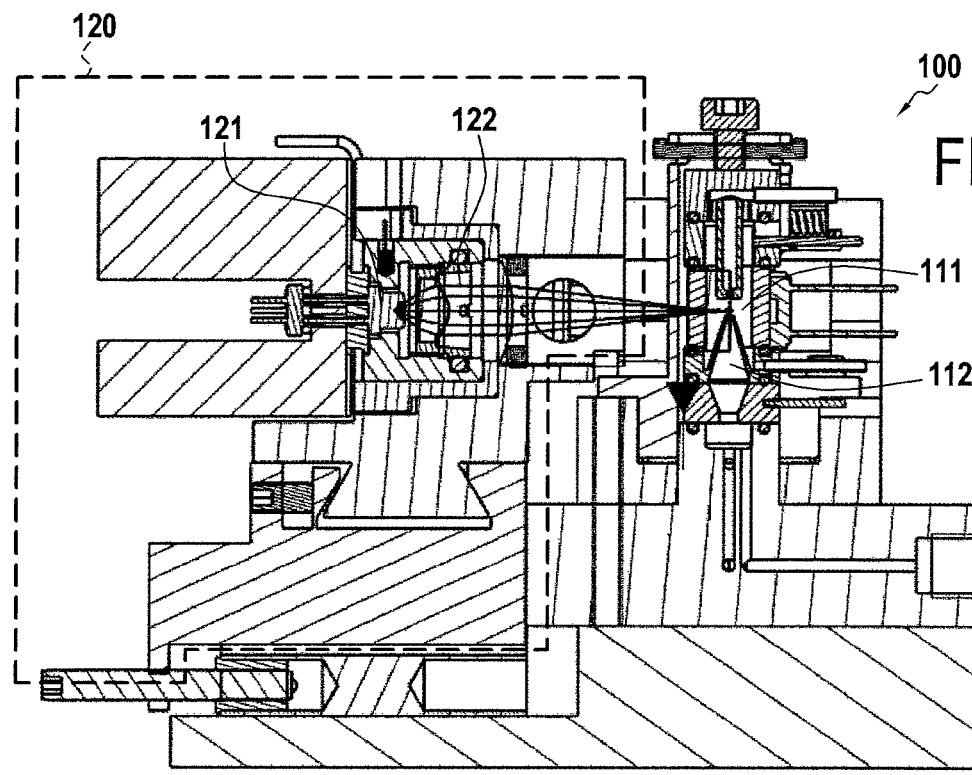
FIG. 3 is a view in section (YZ) of the device from FIG. 1.

FIG. 3 is a view of the device 100 in section on a plane YZ intersecting the measurement plane. The assembly 120 comprises a light source 121 and optics 122 for appropriate illumination of the measurement tank.

It should be pointed out again here that the optical axis of the assembly 120 is perpendicular to the fluid flow direction. The three optical axes of the assemblies 120, 130, and 140 are therefore coplanar and the fluid flow in the measurement tank 111 is perpendicular to this common plane.

Figure 4:
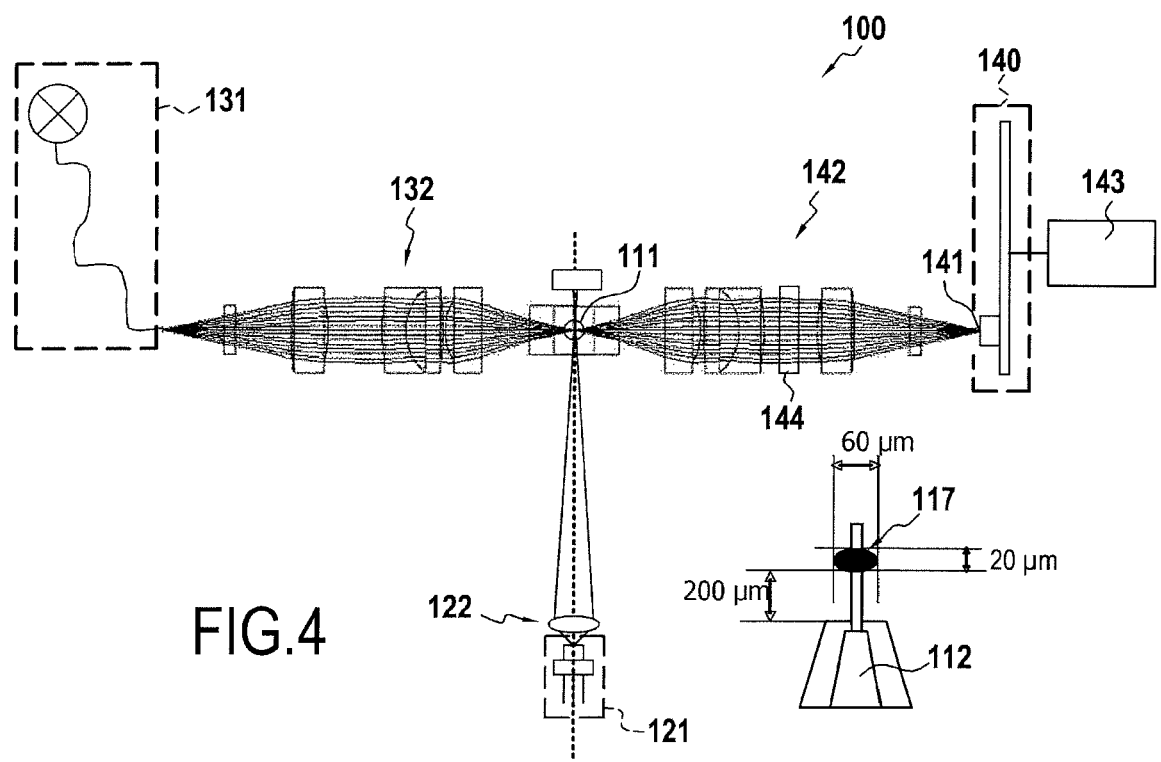
FIG. 4 is a simplified plan view of the FIG. 1 device.

FIG. 4 is a simplified plan view of the device 100 in which the measurement tank 111 is diagrammatically represented with the light sources 121, 131, and the sensor 141.

The two sources 121 and 131 emit at different wavelengths and are used for two types of measurement, absorption measurements and fluorescence measurements. The absorption measurement is a measurement of the apparent absorption that is the sum of diffraction, refraction/reflection and true absorption effects caused by the presence of the cells and in particular the presence of natural or artificial cytochromes of the cells.

The apparent absorption largely involves cellular refringence/diffraction phenomena. For most cells, notably cells of the granulocyte line, it is the granules and the accurate assessment of their size and number that contribute to a high-quality morphometric analysis.

Below a non-limiting embodiment of the invention for measuring fluorescence of Thiazole Orange and measuring absorption is described.

Figure 5:
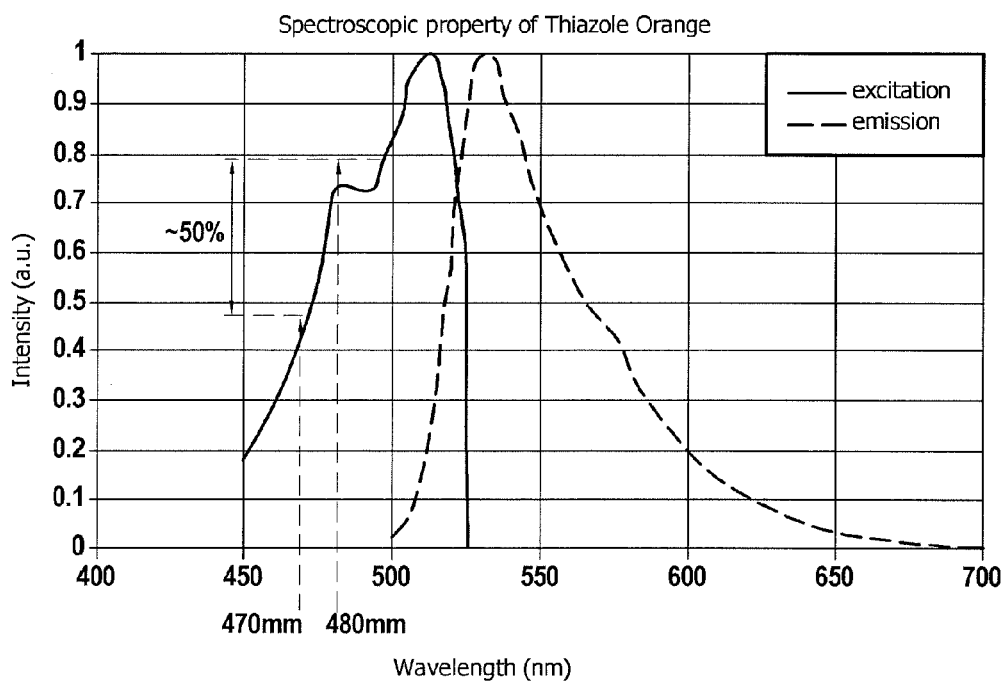
FIG. 5 represents the excitation and fluorescence spectrum of Thiazole Orange.

FIG. 5 represents the spectroscopic properties of Thiazole Orange. Note that the maximum absorption wavelength is around 510 nm. This wavelength being close to the re-emission wavelength, which is situated around 530 nm, it is nevertheless preferable to use a source emitting primarily at the secondary maximum at around 480 nm.

In one embodiment of the invention the light source 121 is a 20 milliwatt (mW) 473 nm laser diode used to excite the cells marked with Thiazole Orange circulating in the measurement tank 111 of the flow cytometer. The fluorescence emitted by each of the cells, proportional to the quantity of nucleic acids that constitute it, is collected at 90° on the optical axis of the sensor 141. To stabilize the wavelength the laser diode 121 is advantageously current-regulated to prevent temperature fluctuations and luminous power fluctuations over time.

It is moreover known that light emitted by a laser diode 121 diverges in a very pronounced way with mid-height width angles reaching 40° on one axis and 10° on another axis perpendicular to the first.

Also, special collimation optics are necessary to remedy the very pronounced divergence of the beam emitted by the laser diode 121. Molded aspherical lenses are conventionally used for this purpose because of their low cost in large quantities. To collect all of the emitted laser beam the numerical aperture of these lenses is generally at least 0.5. Using this type of lens makes it possible to form a collimated beam with low divergence. The as yet elliptical collimated beam may be rendered circular by a pair of anomorphic prisms. This operation consists in compressing the major axis or stretching the minor axis to obtain a circular beam. Note that compressing the major axis is not necessary in the device of the invention as the elliptical shape of the laser diode 121 is not a problem; to the contrary, it favors conforming the beam into an elliptical capture window 117 the size of which 200 micrometers (μm) from the outlet of the injection nozzle 112 is approximately 20×60 square micrometers (μm$^2$) (see FIG. 4).

The second light source 131 advantageously emits at around 650 nm. In one embodiment of the invention this light source is a resonant-cavity light-emitting diode (RCLED).

According to the invention, the sensor 141 is used to measure fluorescence and absorption. It is associated with optics 142 also used for fluorescence and for absorption.

The sensor 141 is connected to an electronic control circuit 143 adapted to modify its gain.

In the embodiment of the invention described here, the sensor 141 is an avalanche photodiode the bias of which is modified by the control circuit 143 so that the photodiode 141 operates according to the principles of the invention.

The invention uses the control circuit 143 to inhibit the avalanche gain to configure the avalanche photodiode as a simple photodiode. Thus the avalanche photodiode has a switchable gain. This is a novel and previously unpublished mode of using an avalanche diode.

The benefit of the invention is to use only one sensor device for characterizing and counting blood elements. A cost saving is obtained as duplicated detection channels are not used for each measurement (absorbance and fluorescence).

Figure 6:
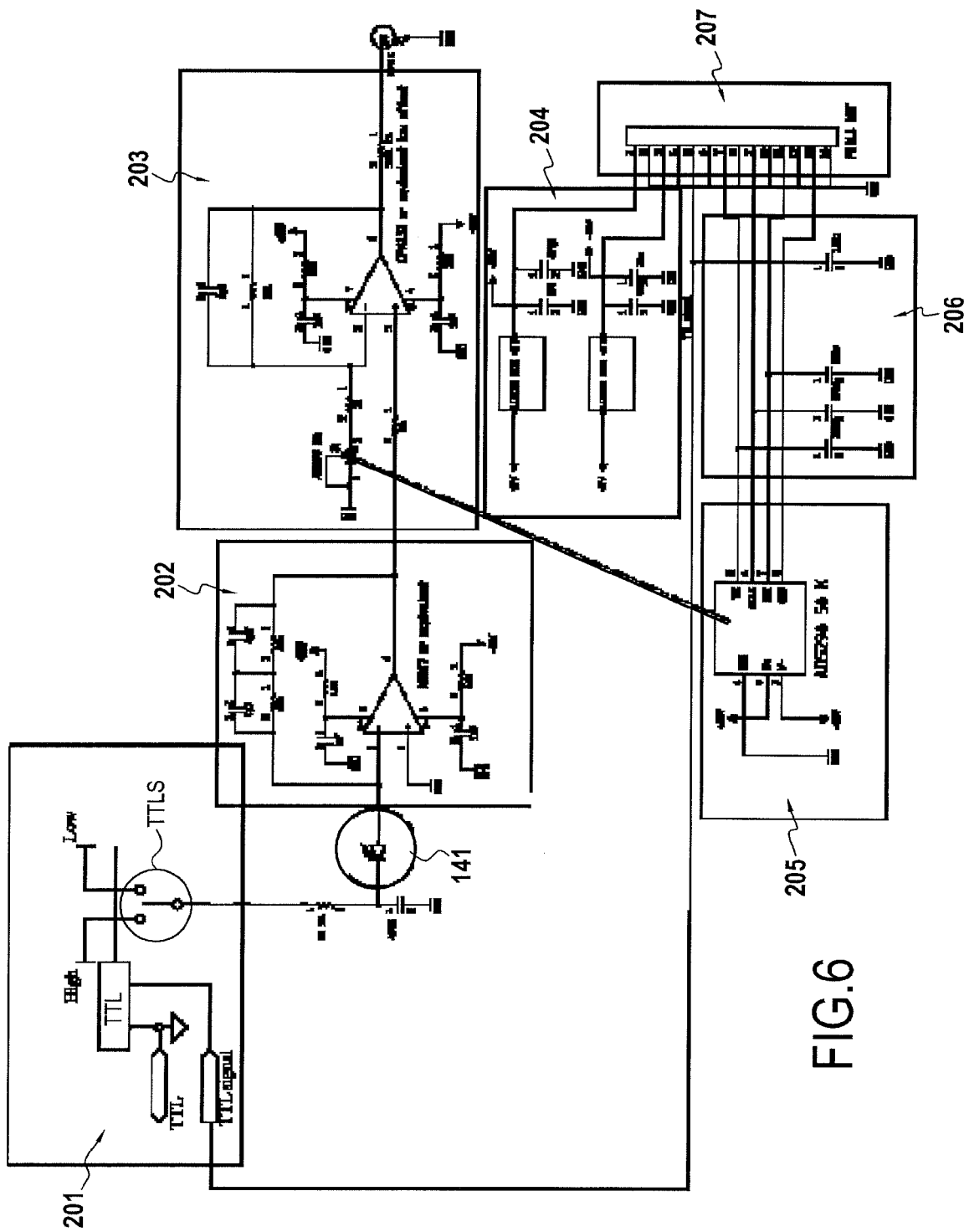
FIG. 6 is a diagram of the electronic control circuit connected to the sensor in one embodiment of the invention.

FIG. 6 is a functional block diagram of the structure of the control circuit 143 for controlling the photodiode 141. This circuit 143 has a programmable voltage source capable of generating low and high voltages.

Two digital controls in the circuit 143 are used to set the detection sensitivity and gain parameters of the photodiode 141, which is a Hamamatsu S5343, for example.

As represented by the functional block 201, the avalanche gain M is controlled by a TTLS 1-digit digital control corresponding to a two-position switch. This gain, also referred to as the internal gain, determines the sensitivity of the receiver, i.e. the smallest quantity of photons that it can detect.

When TTLS=1, the so-called high voltage, equal to 150 volts (v), for example, biases the junction in avalanche mode, conferring on the sensor an internal gain M greater than 1, for example M=60; the sensitivity of the sensor is then a maximum sensitivity, typically 10 picowatts (pW).

In avalanche mode, the reverse voltage is adjusted to obtain a gain compatible with the level or levels of fluorescence to be detected. In a preferred embodiment of the invention the voltages are regulated around their nominal value to take account of variations in the temperature of the enclosure in which the component 141 operates. This voltage regulation makes it possible to stabilize the gain at its nominal value, typically of the order of 60, over a given range of temperatures that run from 25° C. to 40° C.

When TTLS=0, the so-called low voltage, for example 15 volts, biases the junction in photodiode mode, with no gain (M=1), in which the sensitivity of the receiver is of the order of 1 nanowatt (nW).

The bias voltages used may of course vary as a function of the diode used. For the type of diode used in the present embodiment, a non-zero voltage below 30 V, at which the avalanche effect begins, may be chosen to provide unity gain. In contrast, as the junction capacitance increases very quickly below 15 V, it is preferable to choose a voltage not significantly lower than this value to obtain operation in the frequency ranges concerned.

As low voltages, typically of the order of 10 to 20 V, the space charge zone is small even within the PN junction. Amplification by the avalanche effect is therefore substantially inhibited and the component 141 functions as a simple photodiode.

Setting the bias voltage to a non-zero value with a view to reducing the electrical capacitance in picofarads (pF) of the photodiode junction to a sufficient value confers on the sensor 141 a bandwidth compatible with detection of short light pulses, the duration of which is typically 10 microseconds (µs). This voltage must nevertheless remain sufficiently low to prevent internal amplification in the photodiode.

The reduction in the junction capacitance is necessary to confer on the sensor an optimum bandwidth compatible with the analysis of signals from the analysis system. These signals are random pulse trains.

The requirement for temporal resolution and the necessity of analyzing signals deformed very little by the receiver circuit imposes a bandwidth $F_p$>Fco where Fco is the minimum cut off frequency such that a pulse is not significantly deformed. In practice, Fco is equal to 350 kilohertz (kHz), for example.

In this operating mode in which the avalanche effect is inhibited, the sensor 141 is used to measure the apparent absorption of the cells. For example, hemoglobin is a natural cytochrome of erythrocytes. Eosin is an artificial cytochrome that can be fixed by leucocytes by the method described in the patent EP 0 430 750, for example.

A different embodiment of the invention could use a programmable or otherwise controllable voltage generator. The reverse voltage applied to the avalanche photodiode 141 could be controlled by digital or analog means to control its internal gain and thus the sensitivity of the receiver.

Whatever its bias mode, the photodiode is coupled to a transimpedance amplifier block 202 for converting the photocurrent into a voltage.

In an advantageous embodiment of the invention, the transimpedance gain is equal to 300 kilohms (kΩ). The output voltage is ±15 V in order to achieve a sufficient output dynamic range. In particular, a wide dynamic range is necessary for precise absorption measurements.

Absorption measurements consist in observing the light loss δI from a continuous component I. The analysis signal δI=σI where σ is the fraction of light lost by absorption by the analyzed particle. With a receiver limited by photo-electric noise, the mean-square noise value is equal to b=√2qIB where q is the charge on the electron and B is the bandwidth of the receiver circuit.

The signal-to-noise ratio is $$\delta I/b = \sigma I/\sqrt{2qIB} = (\sigma/\sqrt{2qB})\sqrt{I}.$$

This formula indicates that the signal-to-noise ratio increases with √I, whence the necessity of using the highest luminous flux value. This luminous flux may nevertheless not be greater than a certain value Î defined by the equation RηÎ=Vs where R is a trans-impedance gain, η is the quantum yield of the sensor at the illumination wavelength, and Vs is the saturation voltage of the first amplifier. Typical values given here by way of example, Vs=12 V, R=300 kilohms, η=0.6 amps per watt (A/W) at 650 nm make it possible to calculate Î=67 microwatts (µW). The detection limit defined by the criterion δI/b=1 then makes it possible to determine the detectable light fraction σ:

$$\sigma = \sqrt{2qB/\hat{I}} = 4.10^{-5}$$

The smallest effective absorption section that it is possible to detect is then equal to $$\sigma' = \sigma \cdot (a \cdot b) = 0.1 \, \mu m^2,$$

where a and b are respectively the height and the width of the measurement window, which is compatible with the detection of small elements such as platelets.

In avalanche mode the sensitivity is the optimum sensitivity and the sensitivity of the receiver circuit is given by the characteristics of the photodiode, notably its noise equivalent power (NEP), of the order of 10 pW, obtained in avalanche mode for M=60.

The block 203 conditions the signal from the first stage 202 within the range of the downstream circuit. The block 203 makes it possible to adjust the voltage to the input dynamic range of an analog-digital converter or a processor circuit. The signal is conditioned by optimum adjustment of the gain of the amplifier. Here the amplifier is a non-inverting operational amplifier for which the closed-loop gain is given by G=(1+r/R) where r is the feedback resistance and R is the equivalent resistance of the branch between the non-inverting input and ground. The gain G is advantageously variable in a ratio 1:5 and makes it possible to increase further the light detection sensitivity.

Note here that the resistor R is controlled digitally, which is propitious for remote control by means of a microcontroller, for example, the block 205 comprising an off-the-shelf AD5290 digital potentiometer in the embodiment of the invention represented in FIG. 5. The position of this resistor R is not immaterial as this arrangement preserves the bandwidth of the circuit.

The block 204 comprises filtered and regulated voltage supplies for the control circuit 143.

The block 206 includes decoupling capacitors for filtering unwanted signals transported by the control line.

The block 207 is an I/O line electrical interface connector.

The following table of gain values summarizes the adjustment values of the gains M and G used for the analysis of different types of aliquots contained in the blood:

| Analysis cycle | M | G |
|---|---|---|
| LMNE | 1 | 3 |
| GR/PLT | 1 | 5 |
| BASO | 1 | 2 |
| RETIC | 60 | 5 |
| ERB | 60 | 1 |

A sequence of analysis cycles and operations conducted with the device of the invention and under specific conditions to obtain all of the above populations is described below.

Generally speaking, for a fluorescence measurement, the APD gain is switched to the "M=60" position, after which the laser diode 121 is turned on. The light source 131 is turned off. For an absorption measurement, the APD gain is switched to the "M=1" position, after which the RCLED is turned on. The laser diode is turned off. It is advantageous to envisage placing a dichroic filter on the emission fiber of the RCLED to reflect the fluorescence toward the receiver.

The blood of the patient is sampled in an etda tube. This blood sample is then divided into a plurality of aliquots to be treated differently according to the reagent used to obtain the expected results.

Figure 8C:
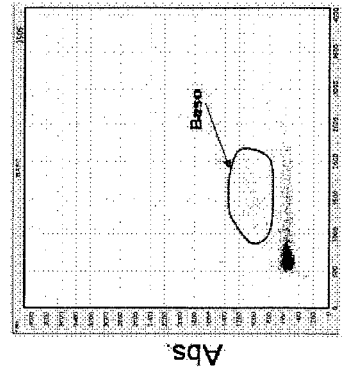
FIG. 8 is a representation of various results that may be obtained using the device.
Figure 8B:
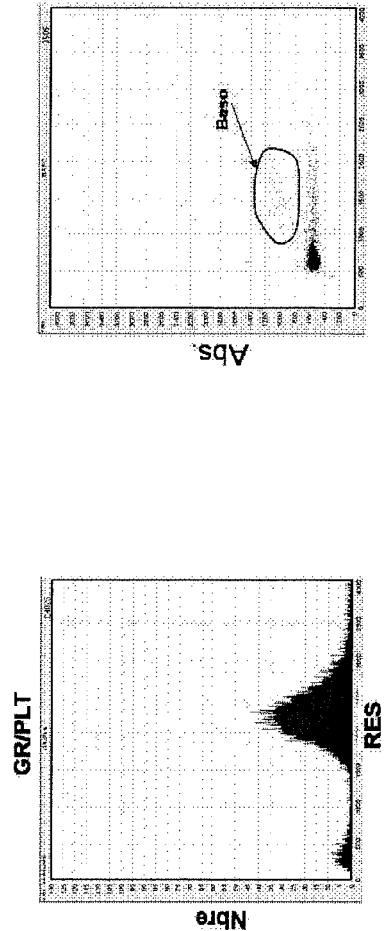
Figure 8A:
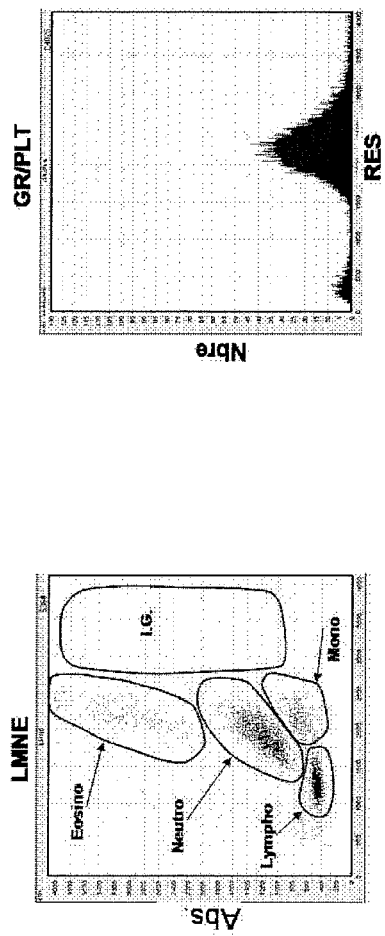

The aliquot LMNE is an aliquot into which has been introduced a reagent such as that described by the applicant in the patent EP 1 239 283. This reagent is adapted to produce lysis of the red cells and enables differentiation and counting of lymphocytes, monocytes, neutrophils and eosinophils by means of absorption and impedance measurement. Here 15 microliters (μL) of blood are mixed with 1.8 milliliters (mL) of the reagent. The gain M of the photodiode is then 1. This preserves the quantitative character of the photodiode for absorption. The electronic gain of the operational amplifier is advantageously slightly higher than that used for basophils, for example 3. The various cell populations may be represented as in FIG. 8a, in which the locations of any immature granules is also shown.

The GR/PLT aliquot is an aliquot into which a reagent such as that described by the applicant in the patent EP 0 856 735 has been introduced. This reagent is adapted to sign red cells and platelets by measuring absorption and impedance. 8 μL of blood are mixed with 2.8 mL of reagent. The gain M of the photodiode is then set to 1, again to preserve its quantitative nature for measuring absorption. The electronic gain G of the operational amplifier is advantageously higher than used for white cells, for example 5. The number of red cells and platelets may be represented as in FIG. 8b.

The BASO aliquot is an aliquot into which a reagent such as that described in the patent EP 1 039 297 has been introduced. This reagent is adapted to sign basophilic cells by measuring absorption and impedance, as it reduces the volumetric size of leucocytes except basophils, which makes it possible to differentiate them and count them. 15 μL of blood are mixed here with 1.8 mL of the reagent. The gain M of the photodiode is again 1. This preserves the quantitative nature of the photodiode for measuring absorption. The electronic gain G of the operational amplifier is advantageously a low value greater than 1, for example 2. Basophils may thus be represented as in FIG. 8c.

Figure 8E:
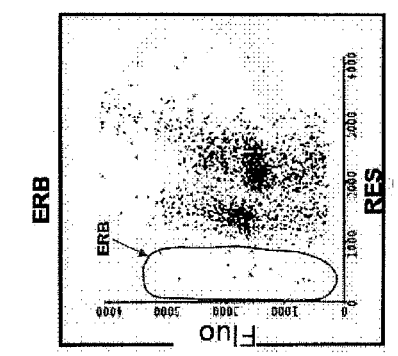
Figure 8D:
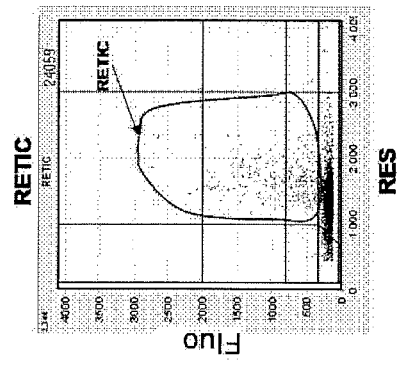

The RET aliquot is an aliquot into which a reagent such as that described in the patent EP 0 856 735 has been introduced to sign reticulocytes by measuring fluorescence. 2.4 μL of blood are here mixed with 2.5 mL of the reagent. The gain M of the photodiode is then maximized to the avalanche gain of the photodiode, here equal to 60. Again, this makes the photodiode sufficiently sensitive for fluorescence measurement. As the expected quantities of light are low, the electronic gain G of the operational amplifier is advantageously maximized, here equal to 5. Reticulocytes are represented as in FIG. 8d, for example. This possibility of measuring reticulocytes is one benefit of the invention because this measurement is of real added value for blood analysis. This measurement is accessible reliably at lower cost by means of the invention. Moreover, the younger the reticulocyte, the greater the quantity of RNA. Because Thiazole Orange reacts in a stoichiometrically statistical manner with the bases of the nucleic acids, the younger the reticulocyte the higher the intensity of the fluorescence. The device of the invention described here and the associated method therefore provide a simple way to classify and quantify reticulocytes at relatively low cost and also to give an indication as to the maturity of these cells.

The ERB aliquot is an aliquot to which a reagent such as described in the patent EP 1 239 283 has been introduced to sign erythroblasts, reticulocyte precursors, by measuring fluorescence. The sample to be analyzed is prepared by mixing 30 μL of blood with 2 mL of reagent. The gain M of the photodiode is then maximized to the avalanche gain of the photodiode, here equal to 60. This makes the photodiode sufficiently sensitive for measuring fluorescence. The electronic gain G of the operational amplifier is 1, for example. This value enables correct quantification of fluorescence in the dynamic range offered in the subsequent processing of the data. Erythroblasts may be represented as in FIG. 8e.

For each of the aliquots obtained with the appropriate reagent, a double measurement (fluorescence and impedance or absorbance and impedance) such as the invention makes possible is effected. This makes it possible, in a specific and sensitive manner, to classify and count the cell populations referred to above, namely erythrocytes, reticulocytes, erythroblasts, platelets, reticulated platelets, and leucocytes, of which there are a plurality of categories identifiable by the invention such as lymphocytes, monocytes, neutrophils, eosinophils and basophils. Thus with the invention ten cell populations are easily identifiable and may be quantified using the five aliquots described above. The fluorescence and absorption measurements with the associated impedance measurements for each of the above prepared mixtures make it possible to distinguish these populations. With the invention, it is possible to count other cell types, including precursors of leucocytes, monoblasts, and lymphoblasts, and immature granules.

Beyond the sensor proper, here consisting of the photodiode, the receiver optical system consists of achromatic doublets. This aperture is sufficient to enable detection of fluorescence coming from the Thiazole Orange coupled to the nucleic acids such as those contained in reticulocytes.

The achromatisation wavelengths are centered on the wavelengths of interest. In one particular embodiment, the absorption of the cell is measured at 650 nm. When using Thiazole Orange, the maximum fluorescence is emitted at the wavelength of 530 nm. A doublet optimized for the wavelengths of 530 nm and 650 nm enables optimum optical focusing on the flow of cells at these two wavelengths.

Also, to be able to detect correctly the quantity of light at the fluorescence and absorption wavelengths, the optical system 142 is corrected for chromatic aberration at 530 nm, the fluorescence wavelength, and at 650 nm, the absorption wavelength.

An absorbant filter 144, for example a Schott GG495 filter, the thickness of which is of the order of 3 mm, is installed in the receiver tubes in the part of the set-up in which the light beam is parallel. This filter 144 absorbs laser light diffracted at a right angle from the laser beam.

Figure 7:
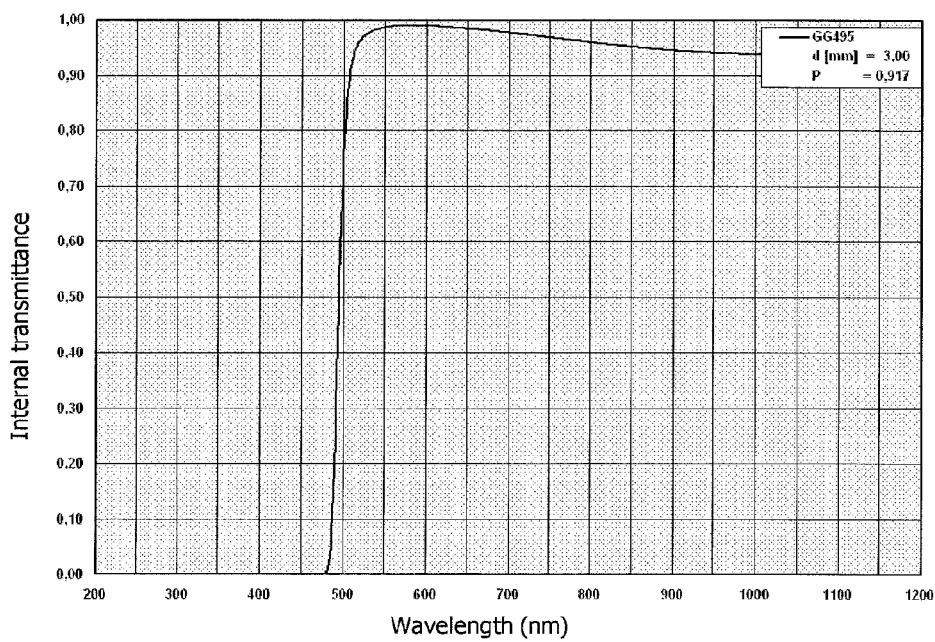
FIG. 7 represents the high-pass transmission of the colored glass optical filter used in a preferred embodiment of the invention.

FIG. 7 represents the high-pass transmission characteristic of the filter 144. It is clear that by emitting at around 470 nm instead of 488 nm, the wavelength of the secondary absorption maximum of Thiazole Orange, it is possible to use this kind of simple and relatively low-cost filter 144, which begins to allow light to pass at around 480 nm. It is in fact a simple colored glass, and effective colored glasses are rare in the light spectrum. It is of course possible to implement the invention at 488 nm, but (at least at present) this leads to additional costs.

Thus for emission at around 488 nm, the use of another type of glass (such as GG510 or OG515 glass) would be desirable to avoid large diffraction angles in the direction of the sensor device. By exciting Thiazole Orange at around 470 nm in the device of the invention, it is found that a luminous efficiency is obtained that is lower than at 488 nm but effective, even though it uses a relatively low-cost colored glass, which is highly advantageous.

This feature further allows reduction of the cost of installing fluorescence measurement in the device of the invention. This filter 144 has a wide-band (between 400 nm and 700 nm) antireflection treatment to reduce Fresnel reflection.

The 473 nm ray from the laser diode 121 is totally absorbed by the filter. Only the fluorescence, with an emission band between 500 nm and 600 nm, and the 650 nm ray from the light source 131 are transmitted.

Here the optics are advantageously corrected for third order aberrations, notably to correct geometrical and chromatic aberrations introduced by the plane (water and glass) refracting surfaces of the measurement chamber 111.

In the final analysis, the device shown makes it possible to image the flow of cells onto the pupil of the sensor 141. The optical resolution in this plane is given by the formula:

$$R=\lambda/(NAe+NAr)$$

in which $\lambda$ is the illumination wavelength and NAe and NAr are respectively the numerical apertures of the illumination and reception beams.

Although the measurement effected in the image plane is purely photometric, the sensitivity of the sensor 141, its capacity to discriminate two cells differentiated by their heterogeneities, is strongly linked to the parameter R, notably the measurement signal-to-noise ratio.

For optimum leucocyte differentiation, at the wavelength of 0.65 µm, it has been observed that the parameter R needs to be less than or equal to 1 µm. This imposes numerical aperture constraints NAe+NAr>0.65. In one embodiment of the invention, the emission and reception apertures are equal and advantageously NAe=NAr≥0.325. In an advantageous embodiment, this aperture is fixed at 0.35.

Finally, the absorption spectrum of peroxidase, an enzyme present in eosinophils that absorbs at 650 nm, contributes to improving separation with neutrophils. In this sense, the invention significantly improves neutrophil/eosinophil separation relative to devices developed in the past.

Clearly the device may be used with other reagents and with relatively different processes to obtain similar results. Other reagents may also be developed for distinguishing and counting cell types other than T, B or NK lymphocytes. Such a reagent could then include an immunological probe consisting of a chemically fluorescent molecule or particle coupled to an antibody. Note that the formulation of the reagent must be such that it enables two-parameter distinguishing as described above.

Note finally that various embodiments may be arrived in accordance with the principles of the invention. In particular, the two light sources may be turned on at the same time to determine biochemical and morphometric properties simultaneously. Despite the sequential nature of the measurements effected by the invention, it has undoubted economic and medical advantages through allowing measurement of fluorescence in devices of relatively low cost which, until now, have enabled only absorption measurements and thus only determination of populations accessible via such measurements.

The invention claimed is:

1. A device (100) for biological analysis by electro-optical measurements on a fluid in a measurement tank (111), said device (100) comprising at least two light sources (121,131) configured to emit in different spectral areas respectively appropriate for measurement of absorption and fluorescence, a means for measuring the impedance associated with each absorption and fluorescence measurement, and a shared detection means (140) comprising three elements being mutualized to enable absorption and/or fluorescence to be measured, said three elements being a sensor (141), an optical system (142), and filter means (144), the internal gain of the sensor (141) being configurable to enable the fluorescence and absorption measurements to be executed sequentially.

2. A device according to claim 1, characterized in that the sensor (141) is an avalanche photodiode connected to a bias circuit (143) adapted to inhibit the internal avalanche gain.

3. A device according to claim 2, characterized in that the inhibited internal gain is 1, the avalanche photodiode (141) behaving as a simple photodiode.

4. A device according to claim 2, characterized in that the bias circuit (143) comprises a two-position switch providing two different voltages, a high voltage and a low voltage, and electrically controlled to provide the high voltage or the low voltage for biasing the photodiode (141).

5. A device according to claim 2, characterized in that the bias circuit (143) comprises a programmable voltage generator controlled by digital or analog means to control the bias voltage applied by this generator to the avalanche photodiode.

6. A device according to claim 1, characterized in that the two light sources (121,131) have emission optical axes coplanar with the optical axis of the light sensor (141).

7. A device according to claim 6, characterized in that the optical axis of the light source (131) emitting at the absorption wavelengths is aligned with that of the light sensor (141) and the optical axis of the light source for exciting fluorescence (121) is perpendicular to the optical axes of the sensor (141) and the other light source (131).

8. A device according to claim 1, characterized in that the sensor (141) is connected to an electronic amplification stage (203) with electronic gain variable as a function of the measurement effected.

9. A device according to claim 8, characterized in that the internal gain of the sensor (141) and the electronic gain are configurable to enable discriminating absorption and fluorescence measurements for a plurality of cell populations chosen from at least basophils, lymphocytes, monocytes, neutrophils, eosinophils, erythrocytes, platelets, erythroblasts, reticulocytes, and reticulated platelets.

10. A device according to claim 8, characterized in that the internal gain of the sensor (141) and the electronic gain are configurable to enable, with the sensor device, discriminating absorption and fluorescence measurements for each analysis cycle, a cycle enabling the classification and the absolute counting of a family of cells present in the sample.

11. A device according to claim 10, characterized in that the internal gain of the sensor (141) and the electronic gain are configurable to enable, with the sensor device, discriminating absorption and fluorescence measurements for at least the analysis cycles of basophils and reticulocytes.

12. A device according to claim 1, characterized in that, for the fluorescence measurement, a fluorescence marker being used is Thiazole Orange, the fluorescence excitation source emits at around 470 nm and the filter means of the sensor device comprise a colored glass-type filter of cut-off wavelength situated in a vicinity of 495 nm.

13. A device according to claim 1, characterized in that the two sources may be turned on simultaneously to obtain biochemical and morphometric data.

14. A method for classifying and counting cell populations present in the biological sample, wherein the method uses the device of claim 1 for classifying and counting the cell populations and comprises the steps of:
    placing a fluid in the measurement tank, the fluid comprising cell populations present in a biological sample,
    emitting light in different spectral areas respectively appropriate for measurement of absorption and/or fluorescence with the at least two light sources,
    measuring the impedance of the cell populations, and
    measuring associated absorption and/or fluorescence of the cell populations.

* * * * *